United States Patent

Mylari

Patent Number: 5,304,557
Date of Patent: Apr. 19, 1994

[54] SUBSTITUTED OXOPHTHALAZINYL ACETIC ACIDS AND ANALOGS THEREOF

[75] Inventor: Banavara L. Mylari, Waterford, Conn.

[73] Assignee: Pfizer Inc., New York, N.Y.

[21] Appl. No.: 854,984

[22] PCT Filed: Dec. 15, 1989

[86] PCT No.: PCT/US89/05637

§ 371 Date: Apr. 30, 1992

§ 102(e) Date: Apr. 30, 1992

[51] Int. Cl.[5] .............. C07D 231/56; C07D 403/06; C07D 471/04; A61K 31/415

[52] U.S. Cl. .................. 514/248; 514/249; 514/403; 544/236; 544/237; 548/362.5

[58] Field of Search ............ 544/236, 237; 548/371; 514/248, 249, 403

[56] References Cited

U.S. PATENT DOCUMENTS

| | | | |
|---|---|---|---|
| 4,251,528 | 2/1981 | Brittain et al. | 424/250 |
| 4,868,301 | 9/1989 | Mylari et al. | 544/237 |
| 4,904,478 | 2/1990 | Sinay, Jr. et al. | 544/237 |
| 4,939,140 | 7/1990 | Larson | 544/237 |

FOREIGN PATENT DOCUMENTS

| | | |
|---|---|---|
| 0002895 | 7/1979 | European Pat. Off. |
| 222576 | 5/1987 | European Pat. Off. |
| 0295051 | 12/1988 | European Pat. Off. |
| 0033134 | 9/1989 | European Pat. Off. |

*Primary Examiner*—Mark L. Berch
*Attorney, Agent, or Firm*—Peter C. Richardson; Paul H. Ginsburg

[57] ABSTRACT

A compound of the formula

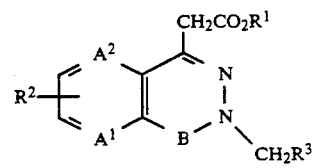

wherein
$A^1$ and $A^2$ are independently N or CH;
B is a covalent bond or C=O;
$R^1$ is hydrogen or $C_1-C_6$ alkyl;
$R^2$ is hydrogen, fluorine, chlorine, bromine, trifluoromethyl, $C_1-C_4$ alkyl, $C_1-C_4$ alkoxy, or $C_1-C_4$ alkylthio;
$R^3$ is

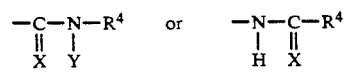

wherein
$R^4$ is phenyl optionally substituted;
X is oxygen or sulphur;
Y is hydrogen; or Y forms an indole group with the carbon on the ortho position of the phenyl in $R^4$; or a pharmaceutically acceptable base salt thereof when R is hydrogen;

with the proviso that when B is a covalent bond, $A^1$ and $A^2$ are each CH, and use for the inhibition of aldose reductase activity.

12 Claims, No Drawings

SUBSTITUTED OXOPHTHALAZINYL ACETIC ACIDS AND ANALOGS THEREOF

BACKGROUND OF THE INVENTION

This invention relates to novel substituted oxophthalazinyl acetic acids having aldose reductase inhibitory activity useful in the treatment of chronic complications arising from diabetes mellitus, such as diabetic cataracts, retinopathy and neuropathy, to pharmaceutical compositions containing such compounds and to a method of using such compounds.

The use of aldose reductase inhibitors in the treatment of complications of diabetes is known from European Patent Publication No. 222,576, published May 20, 1987, disclosing heterocyclic oxophthalazinyl acetic acids.

SUMMARY OF THE INVENTION

According to the invention, a compound is provided having the formula

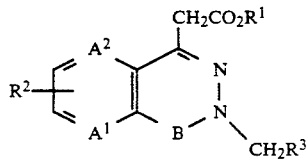

wherein $A^1$ and $A^2$ are independently N or CH; B is a covalent bond or C=O; $R^1$ is hydrogen or $C_1$-$C_6$ alkyl; $R^2$ is hydrogen, fluorine, chlorine, bromine, trifluoromethyl, $C_1$-$C_4$ alkyl, $C_1$-$C_4$ alkoxy, or $C_1$-$C_4$ alkylthio; $R^3$ is

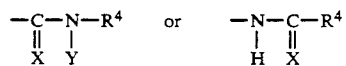

wherein $R^4$ is phenyl optionally independently substituted by one or two of fluoro, chloro, bromo, trifluoromethyl, trifluoromethylthio, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, or nitro; with the proviso that when $R^4$ is disubstituted phenyl, the substitution is at the 3 and 4, or the 3 and 5, or the 2 and 5 positions in the phenyl moiety; X is oxygen or sulphur; Y is hydrogen; or Y forms an indole group with the carbon on the ortho position of the phenyl moiety in $R^4$; or a pharmaceutically acceptable base salt thereof when $R^1$ is hydrogen; with the proviso that when B is a covalent bond, $A^1$ and $A^2$ are each CH.

In a preferred embodiment of the invention, $A^1$ and $A^2$ are each CH. In another preferred embodiment, B is C=O. In yet another preferred embodiment, $R^4$ is phenyl substituted by at least one of chloro, bromo, or trifluoromethyl.

The present invention also relates to a composition for inhibition of aldose reductase activity comprising a compound of formula I in an amount effective in the inhibition of aldose reductase activity, in admixture with a pharmaceutically acceptable carrier. Preferred compositions contain the preferred compounds of formula I as described above.

The invention further comprises a method of treating a diabetic host such as an animal or a human for diabetes-associated complications, which comprises administering to the host an effective amount of a compound of formula I. Preferred methods comprise administering the preferred compound of formula I as described above.

DETAILED DESCRIPTION OF THE INVENTION

The term "alkyl" whenever used in the definitions of $R^1$, $R^2$, $R^3$, etc., denotes saturated monovalent straight or branched aliphatic hydrocarbon radicals, such as methyl, ethyl, propyl, t-butyl, etc.

The compounds of formula I wherein $R^3$ is —C(=X)—$NYR^4$ may be prepared by reacting a compound of the formula

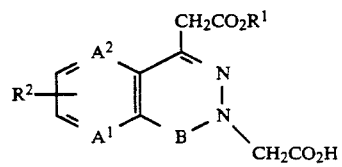

wherein $A^1$, $A^2$, B and $R^2$ are as defined above with reference to formula I, and $R^1$ is $C_1$-$C_6$ alkyl, with a compound of the formula

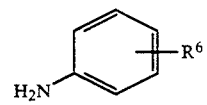

wherein $R^6$ is one or two of fluoro, chloro, bromo, trifluoromethyl, trifluoromethylthio, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, or nitro, with the proviso that when $R^6$ is a disubstituent, the substitution is at the 3 and 4, or the 3 and 5, or the 2 and 5 positions in the aniline derivative of formula III. This condensation reaction proceeds under process conditions conventional for the formation of peptide bonds by coupling of a carboxylic acid and an amine. Thus, the reaction is generally conducted in the presence of a coupling agent such as isobutylchloroformate, dicyclohexylcarbodiimide or anhydroxy succinimide. The reaction is conveniently carried out in a reaction inert solvent. Suitable solvents are halocarbon solvents such as chloroform or methylene chloride. The reaction may be conducted at temperatures ranging from about 20° to about 60° C., usually about room temperature.

The compounds of formula II may be prepared from compounds of the formula

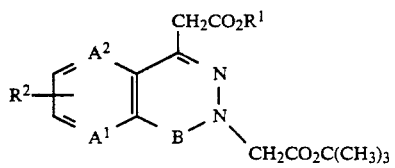

by hydrolysis with an acid such as concentrated sulfuric acid or trifluoroacetic acid. The compounds of formula IV may be prepared from compounds of the formula

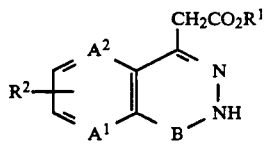

wherein $A^1$, $A^2$, B and $R^2$ are as defined above with reference to formula I, and $R^1$ is $C_1$-$C_6$ alkyl, by reaction with $HalCH_2CO_2C(CH_3)_3$ wherein Hal is chloro, bromo or iodo. This reaction takes place in the presence of a base. Suitable bases are alkali metal t-butoxide such as potassium t-butoxide, alkali metal hydride such as sodium hydride, or alkali metal carbonate such as potassium carbonate. The reaction is conducted in the presence of a solvent such as dimethylacetamide)acetone or diglyme. The reaction temperature ranges from about room temperature to about 100° C.

The compounds of formula I wherein $R^3$ is $-NH-C(=Y)-R^4$ may be prepared by reacting a compound of the formula

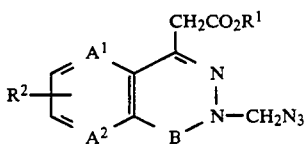

wherein $A^1$, $A^2$, B and $R^2$ are as defined above, and $R^1$ is $C_1$-$C_6$ alkyl, with an anhydride compound of the formula

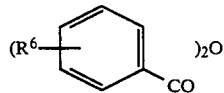

wherein $R^6$ is as defined above with reference to formula III. The reaction is conducted under conventional hydrogenation conditions with hydrogen at pressures ranging from ambient pressure to about 50 p.s.i. Suitable hydrogenation catalysts include palladium, platinum and Raney nickel. Suitable solvents are solvents inert under the reaction conditions such as tetrahydrofuran, ethylacetate, or acetic acid.

The compounds of formula VI may be prepared by reacting a compound of the formula

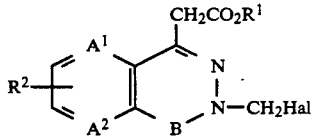

wherein $A^1$, $A^2$, B and $R^2$ are as defined above with reference to formula I, $R^1$ is $C_1$-$C_6$ alkyl, and Hal is chloro, bromo or iodo, with sodium azide or $C_1$-$C_4$ alkyl ammonium azides. Generally, the reaction is conducted in a solvent such as dimethyl formamide or 1-methylpyrrolidinone. The reaction temperatures range from about room temperature to about 60° C.

The compounds of formula I wherein $R^3$ is $-C(=X)-NY-R^4$ may alternatively be prepared by reacting a compound of the formula V with a compound of the formula

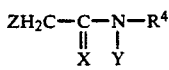

wherein Z is chloro, bromo, iodo, $C_1$-$C_4$ thioalkyl, or $C_1$-$C_4$ alkylsulfonyl, and X, Y and $R^4$ are as defined above with reference to formula I. The reaction is generally conducted in the presence of a base. Specific reaction conditions include reaction with sodium hydrosulfide in dimethylformamide or diglyme, or alkali metal $C_1$-$C_4$ alkoxide, such as sodium methoxide, in a $C_1$-$C_4$ alkanol, dimethylformamide or diglyme. The reaction proceeds generally at about room temperature to about 100° C.

The compounds of formula IX may be prepared by well-known acylation procedures from a compound of the formula $NHYR_4$ wherein Y and $R_4$ are as defined above with haloacetylchloride, wherein halo is chloro, bromo or iodo, or $(C_1$-$C_4)$alkylthioacetylchloride, or $(C_1$-$C_4)$alkylsulfonylacetylchloride. The reaction generally proceeds in the presence of a tertiary amine such as triethylamine.

The compounds of formula I wherein $R^1$ is hydrogen may be prepared from the corresponding compounds of formula I wherein $R^1$ is $C_1$-$C_6$ alkyl by standard hydrolysis. Thus, the hydrolysis proceeds at conventional temperatures and in the presence of acid or base such as a mineral acid, for example, hydrochloric acid, or an alkali metal hydroxide or carbonate such as sodium or potassium hydroxide or carbonate. The reaction is carried out in the presence of water and a solvent, for example an alkanol of 1 to 4 carbon atoms such as methanol, or dioxane.

The compounds of formula I wherein $R_1$ is hydrogen may be esterified by conventional methods such as reaction of the corresponding acid chloride, bromide or anhydride with $R_1H$ to obtain compounds (I) wherein $R_1$ is $C_1$-$C_6$ alkyl.

The compounds of formula I wherein X is sulfur may be prepared by thiating the corresponding compounds (I) wherein X is oxygen by known procedures, for example, by reaction with phosphorus pentasulphide, $P_4S_{10}$, or Lawesson's reagent in an aromatic solvent such as benzene, toluene, xylene, pyridine, or quinoline. The reaction temperature generally ranges from about 50° C. to about the reflux temperature of the solvent used.

The pharmaceutically acceptable base addition salts of compounds (I) wherein $R_1$ is hydrogen may be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired metal and the solution subsequently evaporated to dryness. Suitable pharmaceutically acceptable cations for this purpose include, but are not limited to, alkali metal cations such as potassium and sodium, ammonium or water-soluble amine addition salts such as N-methylglucamine(meglumine), the lower alkanolammonium and other base salts with organic amines which are pharmaceutically acceptable, and alkaline earth metal cations such as calcium and magnesium.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention and alleviation of such conditions. The compound may be administered to a subject in need of treatment by a variety of conventional routes of administration, including orally, parenterally and topically. In general, these compounds will be administered orally or parenterally at dosages between about 0.5 and 25 mg/kg body weight of the subject to be treated per day, preferably from about 1.0 to 10 mg/kg. However, some variation in dosage will necessarily occur depending on the condition of the subject being treated. The person responsible for administration will, in any event, determine the appropriate dose for the individual subject.

The novel compounds of the invention may be administered alone or in combination with pharmaceutically acceptable carriers,, in either single or multiple doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this purpose include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compounds of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitioneal administration. In this connection, the sterile aqueous media employed are all readily available by standard techniques known to those skilled in the art.

Compounds of formula I may not only be advantageously employed for the preparation of aqueous pharmaceutical compositions for parenteral administration, as described above, but more particularly for the preparation of pharmaceutical compositions suitable for use as ophtbalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts, the compounds of this invention are administered to the eye of an ophthalmic preparation prepared in accordance with conventional pharmaceutical practice, see for example "Remington's Pharmaceutical Sciences" 15th Edition, pages 1488 to 1501 (Mack Publishing Co., Easton, Pa). The ophthalmic preparation will contain a compound of formula I or a pharmaceutically acceptable salt thereof in a concentration from about 0.01 to about 1% by weight, preferably from about 0.05 to about 0.5%, in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potassium borate, sodium and potassium carbonate, sodium acetate, sodium biphosphate and the like, in amounts sufficient to maintain the pH at between about 6 to 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example, in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e., diabetic, rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; (5) measuring their ability to delay cataract formation and reduce the severity of lens opacities in chronic galactosemic rats; (6) measuring their ability to prevent sorbitol accumulation and cataract formation in isolated rat lens incubated with glucose; and (7) measuring their ability to reduce already elevated sorbitol levels in isolated rat lens incubated with glucose.

The compounds of formula I wherein $R^3$ is —C(=X-)NYR$^4$ are also of use as intermediates in the preparation of benzothiazolyl compounds of the formula

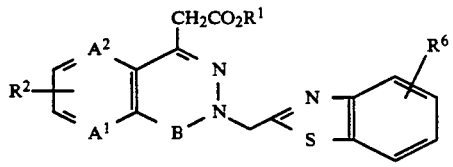

by reaction with sodium hydride in a solvent such as dimethylformamide. The compounds of formula XI are disclosed in European patent publication 222,576. Thus, according to the European patent publication, $R^6$ may include one or two of fluoro, chloro, bromo, trifluoromethyl, trifluoromethylthio, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, or nitro.

The present invention is illustrated by the following examples. It will be understood, however, that the invention is not limited to the specific details of these examples. Proton nuclear magnetic resonance spectra (NMR) were measured for solutions in deuterochloroform (CDCl$_3$) and peak positions are expressed in parts per million (ppm) downfield from tetramethylsilane. The peak shapes are denoted as follows: s, singlet; d, doublet; t, triplet; q, quartet; m, multiplet; br, broad.

EXAMPLE 1

A. 2'-Bromo-5'-trifluoromethyl-2-chloroacetanilide

To a solution of 2-bromo-5-trifluoromethylaniline (10.0 g) in methylene chloride (100 ml) was added triethylamine and the solution was cooled to 0° C. To this solution was slowly added choroacetyl chloride and the reaction mixture was allowed to cool to room temperature overnight. The solution was concentrated and the resulting solid was extracted with ethyl acetate. The organic extract was first washed with 10% HCl (2×2 ml), then with water (12×25 ml) and was collected, dried and evaporated to obtain the title compound (yield, 10.2 g). $^1$HNMR (250 MHz, CDCl$_3$): 4.22 (s, 2 H), 7.26 (d, J=8 Hz, 1 H), 7.66 (d, J=8 Hz, 1 Hz), 8.68 (s, 1 H), 9.02 (br s, 1 H).

In accordance with the above, the compounds in Table 1 were prepared.

TABLE 1

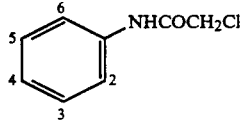

| Entry | Substituent | MP or NMR |
|---|---|---|
| 1 | 2Br, 3CF$_3$, 5CF$_3$ | 139.5–140° C. |
| 2 | 3CF$_3$ | $^1$HNMR(250 MHz, CDCl$_3$): 4.10(s, 2H), 7.26(m, 1H), 7.36(m, 1H)7.50 (M, 1H), 8.2(br s, 1H) |
| 3 | 3Cl | $^1$HNMR(250 MHz, CDCl$_3$): 4.12(s, 2H), 7.06(m, 1H), 7.18(m, 1H)7.32(m, 1H), 8.2(br s, 1H) |

TABLE 1-continued

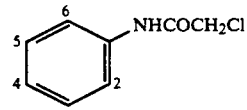

| Entry | Substituent | MP or NMR |
|---|---|---|
| 4 | 4Cl | 167–168° C. |
| 5 | 3F | 119–120° C. |
| 6 | 4CF$_3$ | 153–154° C. |
| 7 | 3CF$_3$, 5CF$_3$ | 85–86° C. |

B. 3-[2-[N-[2-Bromo-5-(trifluoromethyl)phenyl]-amino]-2-oxoethyl]-3, 4-dihydro-4-oxo-1-phthalazineacetic acid ethyl ester.

To a solution of ethyl 4-oxo-3H-phthalazin-1-ylacetate (3.36 g) and potassium t-butoxide (1.62 g) in dimethylformamide (15 ml) was slowly added a solution of 2'-bromo-5'-trifluoromethyl-2-chloroacetanilide (4.55 g) in dimethylformamide (15). After stirring the resulting solution overnight at room temperature, it was poured onto water (50 ml) and the resulting white precipitate was collected and air dried (yield 4.3 g; m.p. 160° C.).

EXAMPLE 2 in accordance with Example 1B, the compounds in Table 2 (X=0) were prepared

TABLE 2

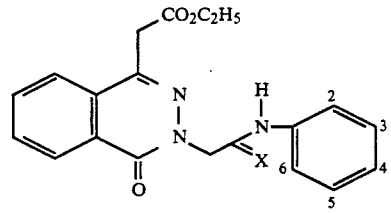

| Entry | X | Ring Substituent | M.P.°C. |
|---|---|---|---|
| 1 | 0 | 2Br, 3CF$_3$, 5CF$_3$ | 195–197 |
| 2 | 0 | 3CF$_3$ | 143 |
| 3 | 0 | 3Cl | 157–158 |
| 4 | 0 | 4Cl | 232–233 |
| 5 | 0 | 3F | 180–181 |
| 6 | 0 | 4CF$_3$ | 196–197 |
| 7 | 0 | 3CF$_3$, 5CF$_3$ | 206–207 |
| 9 | 0 | 2CF$_3$ | 208–209 |
| 10 | 0 | 2Cl | 200–201 |
| 11 | 0 | 2Br, 4OMe, 5CF$_3$ | 215–216 |
| 12 | S | 2Br, 3CF$_3$, 5CF$_3$ | 121–122 |
| 14 | S | 3CF$_3$ | 109–110 |
| 15 | S | 3Cl | 109–111 |

EXAMPLE 3

3-[2-[N-[2-Bromo-5-(trifluoromethyl)-phenyl]amino]-2-oxoethyl]-3, 4-dihydro-4-oxo-1-phthalazineacetic acid To a solution of 3-[2-[N-[2-bromo-5-(trifluoromethyl)phenyl]amino]-2-oxoethyl]-3, 4-dihydro-4-oxo-1-phthalazineacetic acid ethyl ester (1.0 g) in dioxane (10 ml) was added aqueous 20% KOH (2 ml) and the solution was stirred at room temperature for 1 hour. The mixture was concentrated under vacuum, the concentrate was diluted with water (20 ml) and then acidified with concentrated HCl (5 ml). The resulting white precipitate was collected and air-dried (0.7 g; m.p. 200°-202° C.).

EXAMPLE 4

In accordance with Example 3, the compounds in Table 3(X=O) were prepared.

TABLE 3

[Structure: phthalazinone with CH2CO2H at position 1, and N-N-CH2-C(=X)-NH-phenyl substituent; phenyl positions numbered 2,3,4,5,6]

| Entry | X | Ring Substituent | M.P.°C. |
|---|---|---|---|
| 1 | O | 2Br, 3CF3, 5CF3 | 216–217 |
| 2 | O | 3CF3 | 182–183 |
| 3 | O | 3Cl | 204.5 |
| 4 | O | 4Cl | 209–210 |
| 5 | O | 3F | 202–203 |
| 6 | O | 4CF3 | 201–202 |
| 7 | O | 3CF3, 5CF3 | 275(d) |
| 8 | O | 2Br, 5CF3 | 200–202 |
| 9 | O | None | 203 |
| 10 | O | 2CF3 | 208–209(d) |
| 11 | O | 2Cl | 192–193(d) |
| 12 | S | 2Br, 5CF3 | 176–177 |
| 13 | S | 3CF3 | 168–169(d) |
| 14 | S | 3Cl | 179.5–180.5 |

EXAMPLE 5

3-[2-[N-[2-Bromo-5-(trifluoromethyl)phenyl]amino]2-thioxoethyl]-3, 4-dihydro-4-oxo-1-phthalazineacetic acid ethyl ester.

A mixture of 1-phthalazine acetic acid, 3-[2-[N-[2-bromo-5-(trifluoromethyl) phenyl]amino]-2-oxoethyl]-3,4-dihydro-4-oxo, ethyl ester (4.7 g), phosphorus pentasulfide (4.5 g) and benzene (50 ml) was heated until most of the first mentioned starting material had been consumed as determined by TLC monitoring. The reaction mixture was cooled, filtered and filtrate evaporated to dryness. The residue was purified by chromatography over silica gel with methylene chloride as eluent yield, (1.3 g; m.p. 160° C.).

EXAMPLE 6

3-[2-[N-[2-Bromo-5-(trifluoromethyl)-phenyl]amino]-2-thioxoethyl]-3, 4-dihydro-4-oxo-1-phthalazinacetic acid This compound was prepared according to Example 3, starting with 1-phthalazine acetic acid, 3-[2-[N-[2-bromo-5-(trifluoromethyl) phenyl]amino]-2-thioxoethyl]-3,4-dihydro-4-oxo-, ethyl ester (0.15 g) [the final product of Example 5]. The title compound melted at 176°-177° C. (yield, 0.12 g) .

EXAMPLE 7

In accordance with Examples 5 and 6, the compounds in Tables 2 and 3(X=S) were prepared.

EXAMPLE 8

Ethyl
3-(5-trifluoromethylbenzothiazol-2-ylmethyl)-4-oxo-3H-phthalazin-1-ylacetate To a solution of 1-phthalazineacetic acid, -3-[2-[N-[2-bromo-5-(trifluoromethyl) phenyl]amino]-2-thioxoethyl]-3,4-dihydro-4oxo-, ethyl ester (1.3 g) in 1-methyl pyrrolidinone (8 ml) was cautiously added sodium hydride (0.13 g) and then heated at 140° C. for 3 hours. The reaction mixture was cooled to room temperature and then poured onto ice-water (20 ml) containing 10% hydrochloric acid (2 ml). The resulting crude precipitate was filtered and air dried (yield, 1.15 g). A portion of this was crystallized from ethanol to yield the title product, m.p. 131°-132° C.

EXAMPLE 9

In accordance with Example 8, the compounds in Table 4 were prepared.

TABLE 4

[Structure: phthalazinone with CH2CO2C2H5, connected via N-N-CH2- to benzothiazole ring with positions 4,5,6,7]

| Substituent | M.P.°C. |
|---|---|
| 5CF3, 7CF3 | 120–121 |
| 5CF3, 6OCH3 | 212–214 |

EXAMPLE 10

A. Ethyl 2-azidomethyl-4-oxo-3H-phthalazin-1-ylacetate

A mixture of ethyl 2-bromomethyl-4-oxo-3H-phthalazine-1-yl-acetate (2.0 g), sodium azide (0.4 g), acetone (20 ml), water (2 ml) and a catalytic amount of potassium iodide (10 mg) was stirred at room temperature for 4 hours. The mixture was concentrated under vacuum to remove the solvents and obtain the title product as a white solid (1.7 g).

B.
3,4-Dihydro-4-oxo-3-[N-[3-(trifluoromethyl)-benxoyl-]amino]methyl1-phthalazineacetic acid ethly ester To a solution of ethyl 2-azidomethyl-4-oxo-3H-phthalazin-1-ylacetate (1.0 g) and 3-trifluoromethylbenzoic anhydride (2.52 g) in ethyl acetate (50 ml) was added palladium-carbon catalyst (80 mg) and the mixture was hydrogenated at a pressure of 50 psi for 2 hours. The catalyst was filtered off and the filtrate evaporated to a clear oil which solidified upon standing to yield the title product yield (1.6 g) $^1$HNMR (250 MHz, CHCl3): 1.2 (t, J=9 Hz, 3 H), 3.98 (s, 2 H), 4.15 (q, J=9 Hz, 2 H), 5.82 (s, 2 H), 7.4–8.4 (m, 7 H).

EXAMPLE 11

3,4-Dihydro-4-oxo-3-[N-[3-(trifluoromethyl)-benxoyl-]amino]methyl-1-phthalazineacetic acid The title compound was prepared according to Example 3 starting from the compound of Example 10B (1.0 g). The final product melted at 152° dec. (yield, 0.35 g).

EXAMPLE 12

A. 4-Oxo-1,3(4H)-phthalazinediacetic acid 3-(1,1-dimethyl-ethyl) 1-ethyl ester

To a solution of ethyl 4-oxo-3-H-phthalazin-1-ylacetate (46.89 g) in dimethylformamide (DMF) (200 ml) was added potassium t-butoxide (24.7 g) and 1,1-dimethyl-ethyl bromoacetate and the mixture stirrred at room temperature for 1.5 hour. The mixture was quenched with ice-water (500 ml) and extracted with ethyl acetate. The ethyl acetate layer was washed with water (2×200 ml), and the organic extract was dried and then evaporated to dryness to obtain the title compound as a colorless viscous oil (yield, 64.0 g). $^1$HNMR (250 MHz, CDCl$_3$): 1.2 (t, J=6 Hz, 3 H), 1.43 (s, 9 H), 3.95 (s, 2 H), 4.15 (q, J=6 Hz, 2 H), 4.83 (s, 2 H), 7.7 (m, 3 H), 8.4 (m, 1 H).

B. 4-Oxo-1,3(4H)-phthalazinediacetic acid

The compound of Example 12A (64.0 g) was dissolved in concentrated sulfuric acid and stirred at room temperature for 1 hour. The solution was cautiously poured over ice (600 g) and the precipitated solid was collected, washed with water (2×200 ml) and then air-dried. The crude solid was crystallized from ethyl acetate (yield, 39.6 g; m.p. 171° C).

C. 3-[2-[N-[Phenyl]amino]-2-oxoethyl]-3,4-dihydro-4-oxo-1-phthalazineacetic acid ethyl ester To a solution of isobutyl chloroformate (1.37 g) in chloroform (5 ml) was added a solution of the compound of Example 12B (2.90 g) in chloroform (20 ml) and triethylamine (1.01 g ), and the reaction mixture was stirred for 1 hour at 0° C. To this solution was added aniline (0.93 g) and the temperature was allowed to come to room temperature. Evaporation of chloroform gave the title compound as a white solid (yield, 2.81 g; m.p. 187° C.).

EXAMPLE 13

A. Methyl 3-(2,2-diethoxyethyl)-4-oxo-3H-phthalazin1-ylacetate

To a solution containing potassium t-butoxide (5.91 g), methyl 4-oxo-3H-phthalazin-1-ylacetate (10.91 g) and DMF (50 ml) was added bromoacetaldehyde diethylacetal (10.83 g), and the reaction mixture was allowed to stir at room temperature for 48 hours. The reaction mixture was poured onto water, extracted with ethyl acetate and the ethyl acetate layer was collected and dried. Upon evaporation of the solvent, a clear oil was obtained which upon standing gave a white solid (yield, 5.2 g; m.p. 68° C.).

B. Ethyl 3-(5-trifluoromethyl-1,2-dihydrobenzothiazol-2-ylmethyl)-4-oxo-3H-phthalazin-1-ylacetate A mixture of the compound of Example 13A (0.52 g), 2-amino-4-trifluoromethylbenzenethiol hydrochloride (0.50 g) and ethanol (5 ml) was refluxed for 18 hours. The excess ethanol was evaporated and the residue extracted with methylene chloride (2×10 ml). The methylene chloride layer was first washed with 1N hydrochloric acid (5 mi) and then with water (2×10 ml). Evaporation of the methylene chloride layer afforded a light yellow solid. This solid was chromatographed over silica gel and eluted with a mixture of 95:5 methylene chloride and ethyl acetate. The eluent was evaporated to obtain a white solid (yield, 0.3 g; m.p. 134° C.).

C. Ethyl 3-(5-trifluoromethylbenzothiazol-2-yl-methyl)-4-oxo-3H-phthalazin-1-ylacetate To a solution of ethyl 3-(5-trifluoromethyl-1,2-dihydrobenzothiazol-2-y)-4-oxo-3H-phthalazin-1-ylacetate (44 mg) in tetrahydrofuran (5 ml) was added ferric chloride hexahydrate (30 mg) and the reaction mixture was stirred for 14 hours at room temperature. The solution was evaporated to dryness, and the residue was partitioned between ethyl acetate and water. The ethyl acetate layer was collected, dried and evaporated to obtain the title compound (yield, 30 mg; m.p. 133° C.).

I claim:

1. A compound of the formula

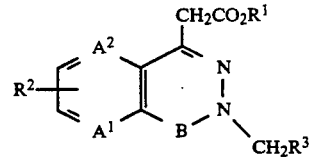

wherein
A$^1$ and A$^2$ are independently N or CH;
B is a covalent bond or C=O;
R$^1$ is hydrogen or C$_1$-C$_6$ alkyl;
R$^2$ is hydrogen, fluorine, chlorine, bromine, trifluoromethyl, C$_1$-C$_4$ alkyl, C$_1$-C$_4$ alkoxy, or C$_1$-C$_4$ alkylthio;
R$^3$ is

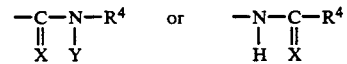

wherein R$^4$ is phenyl optionally independently substituted by one or two of fluoro, chloro, bromo, trifluoromethyl, trifluoromethylthio, C$_1$-C$_4$ alkyl, C$_1$-C$_4$ alkoxy, C$_1$-C$_4$ alkylthio, C$_1$-C$_4$ alkylsulfinyl, C$_1$-C$_4$ alkylsulfonyl, or nitro; with the proviso that when R$^4$ is disubstituted phenyl, the substitution is at the 3 and 4, or the 3 and 5, or the 2 and 5 positions in the phenyl;
X is oxygen or sulphur;
Y is hydrogen; or Y, together with the nitrogen atom to which it is attached, forms an indole group with the carbon on the ortho position of the phenyl in R$^4$; or a pharmaceutically acceptable base salt thereof when R$^1$ is hydrogen;
with the proviso that when B is a covalent bond, A$^1$ and A$^2$ are each CH.

2. A compound according to claim 1 wherein A$^1$ and A$^2$ are each CH.

3. A compound according to claim 1 wherein B is C=O.

4. A compound according to claim 2 wherein B is C=O.

5. A compound according to claim 1 wherein R$^4$ is phenyl substituted by at least one of chloro, bromo or trifluoromethyl.

6. A composition for inhibition of aldose reductase activity comprising a compound according to claim 1 in an amount effective in the inhibition of aldose reductase activity, in admixture with a pharmaceutically acceptable carrier.

7. A composition according to claim 6 wherein A$^1$ and A$^2$ are each CH.

8. A composition according to claim 6 wherein B is C=O.

9. A composition according to claim 7 wherein B is C=O.

10. A composition according to claim 6 wherein R$^4$ is phenyl substituted by at least one of chloro, bromo or trifluoromethyl.

11. A process for the inhibition of aldose reductase activity comprising administering to a diabetic host an effective amount of a compound according to claim 1.

12. A compound according to claim 4 wherein R$^1$ is hydrogen or ethyl, X is oxygen or sulfur and Y is H.

* * * * *